(12) United States Patent
Nappa

(10) Patent No.: US 11,331,525 B2
(45) Date of Patent: *May 17, 2022

(54) COMPOSITIONS COMPRISING 2,3,3,3-TETRAFLUOROPROPENE, 1,1,2,3-TETRA-CHLOROPROPENE, 2-CHLORO-3,3,3-TRIFLUOROPROPENE, OR 2-CHLORO-1,1,1,2-TETRAFLUOROPROPANE

(71) Applicant: THE CHEMOURS COMPANY FC, LLC, Wilmington, DE (US)

(72) Inventor: Mario Joseph Nappa, Leesburg, FL (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/880,194

(22) Filed: May 21, 2020

(65) Prior Publication Data

US 2020/0282249 A1    Sep. 10, 2020

Related U.S. Application Data

(63) Continuation of application No. 15/936,720, filed on Mar. 27, 2018, now Pat. No. 10,688,329, which is a
(Continued)

(51) Int. Cl.
   B24D 18/00    (2006.01)
   A62D 1/00     (2006.01)
   (Continued)

(52) U.S. Cl.
   CPC .............. *A62D 1/00* (2013.01); *C07C 17/25* (2013.01); *C08J 9/144* (2013.01); *C08J 9/146* (2013.01);
   (Continued)

(58) Field of Classification Search
   USPC ................... 51/296, 293, 306, 307
   See application file for complete search history.

(56) References Cited

U.S. PATENT DOCUMENTS 5,036,036 A    7/1991 Lerou
7,641,809 B2   1/2010 Leck et al.
(Continued)

FOREIGN PATENT DOCUMENTS

CA    2 681 872 A1    10/2008
EP    2 080 748 A2    7/2009
(Continued)

OTHER PUBLICATIONS

International Search Report, PCT/US2010/061716, dated May 7, 2011.
(Continued)

*Primary Examiner* — James E McDonough

(57) ABSTRACT

The present disclosure relates to compositions comprising 2,3,3,3-tetrafluoropropene that may be useful as heat transfer compositions, aerosol propellants, foaming agents, blowing agents, solvents, cleaning agents, carrier fluids, displacement drying agents, buffing abrasion agents, polymerization media, expansion agents for polyolefins and polyurethane, gaseous dielectrics, extinguishing agents, and fire suppression agents in liquid or gaseous form. Additionally, the present disclosure relates to compositions comprising 1,1,2,3-tetrachloropropene, 2-chloro-3,3,3-trifluoropropene, or 2-chloro-1,1,1,2-tetrafluoropropane, which may be useful in processes to produce 2,3,3,3-tetrafluoropropene.

9 Claims, 1 Drawing Sheet

Related U.S. Application Data continuation of application No. 14/710,733, filed on May 13, 2015, now Pat. No. 9,943,717, which is a continuation of application No. 13/513,237, filed as application No. PCT/US2010/061716 on Dec. 22, 2010, now Pat. No. 9,051,500.

(60) Provisional application No. 61/289,027, filed on Dec. 22, 2009.

(51) Int. Cl.

| | | |
|---|---|---|
| C09K 3/30 | (2006.01) | |
| C09K 5/04 | (2006.01) | |
| C08J 9/14 | (2006.01) | |
| C09K 23/00 | (2022.01) | |
| C07C 17/25 | (2006.01) | |
| C09K 3/00 | (2006.01) | |
| C09K 3/14 | (2006.01) | |
| C09K 21/08 | (2006.01) | |
| C11D 7/30 | (2006.01) | |
| F25B 39/02 | (2006.01) | |
| H01B 3/56 | (2006.01) | |
| F28C 3/08 | (2006.01) | |
| C11D 7/50 | (2006.01) | |
| B24D 3/00 | (2006.01) | |
| B24D 3/02 | (2006.01) | |
| B24D 11/00 | (2006.01) | |

(52) U.S. Cl.
CPC ............... *C08J 9/149* (2013.01); *C09K 3/00* (2013.01); *C09K 3/14* (2013.01); *C09K 3/30* (2013.01); *C09K 5/044* (2013.01); *C09K 5/045* (2013.01); *C09K 21/08* (2013.01); *C09K 23/017* (2022.01); *C11D 7/30* (2013.01); *C11D 7/5018* (2013.01); *F25B 39/02* (2013.01); *F28C 3/08* (2013.01); *H01B 3/56* (2013.01); *C08J 2203/142* (2013.01); *C08J 2203/162* (2013.01); *C08J 2203/182* (2013.01); *C08J 2300/22* (2013.01); *C08J 2300/24* (2013.01); *C08J 2323/06* (2013.01); *C08J 2323/12* (2013.01); *C08J 2325/06* (2013.01); *C08J 2361/04* (2013.01); *C08J 2375/04* (2013.01); *C09K 2205/122* (2013.01); *C09K 2205/126* (2013.01)

(56) References Cited

U.S. PATENT DOCUMENTS

| | | |
|---|---|---|
| 8,058,486 B2 | 11/2011 | Merkel et al. |
| 9,051,500 B2 | 6/2015 | Nappa |
| 9,943,717 B2 | 4/2018 | Nappa |
| 10,688,329 B2 * | 6/2020 | Nappa .................... F25B 39/02 |
| 2005/0211949 A1 | 9/2005 | Bivens et al. |
| 2005/0228202 A1 | 10/2005 | Nappa et al. |
| 2005/0230657 A1 | 10/2005 | Leek et al. |
| 2005/0233932 A1 | 10/2005 | Singh et al. |
| 2006/0243944 A1 * | 11/2006 | Minor .................... C09K 3/30 |
| | | 252/67 |
| 2007/0100175 A1 | 5/2007 | Miller et al. |
| 2007/0197842 A1 | 8/2007 | Mukhopadhyay et al. |
| 2008/0058562 A1 | 3/2008 | Petrov et al. |
| 2008/0135800 A1 | 6/2008 | Bowman et al. |
| 2008/0230738 A1 | 9/2008 | Minor et al. |
| 2009/0030247 A1 | 1/2009 | Johnson et al. |
| 2009/0182179 A1 * | 7/2009 | Merkel .................. C07C 17/087 |
| | | 570/168 |
| 2009/0204443 A1 | 8/2009 | Tucker et al. |
| 2009/0211988 A1 | 8/2009 | Pham et al. |
| 2009/0224207 A1 | 9/2009 | Pham et al. |
| 2009/0227822 A1 * | 9/2009 | Pham .................... C11D 7/5054 |
| | | 570/178 |
| 2009/0240090 A1 | 9/2009 | Merkel et al. |
| 2009/0242832 A1 | 10/2009 | Pham et al. |
| 2009/0253820 A1 | 10/2009 | Bowman et al. |
| 2009/0278075 A1 * | 11/2009 | Mahler .................... C08J 9/149 |
| | | 252/67 |
| 2009/0287026 A1 | 11/2009 | Kapkalli et al. |
| 2009/0305876 A1 | 12/2009 | Singh et al. |
| 2009/0312585 A1 | 12/2009 | Merkel et al. |
| 2010/0032610 A1 | 2/2010 | Nappa et al. |
| 2010/0036179 A1 * | 2/2010 | Merkel .................. C07C 17/087 |
| | | 570/156 |
| 2010/0154419 A1 | 6/2010 | Kontomaris |
| 2010/0331583 A1 * | 12/2010 | Johnson ................ C07C 17/087 |
| | | 570/156 |
| 2011/0031436 A1 * | 2/2011 | Mahler .................. C07C 17/206 |
| | | 252/78.1 |
| 2012/0222448 A1 * | 9/2012 | Chaki .................... C07C 17/383 |
| | | 62/617 |
| 2016/0168348 A1 | 6/2016 | Golini et al. |
| 2018/0214727 A1 | 8/2018 | Nappa |

FOREIGN PATENT DOCUMENTS

| | | | |
|---|---|---|---|
| EP | 2 103 587 A2 | 9/2009 | |
| EP | 2 107 048 B1 | 7/2019 | |
| WO | 2004/037913 A2 | 5/2004 | |
| WO | 2005/105947 A2 | 11/2005 | |
| WO | 2005/108523 A1 | 11/2005 | |
| WO | 2007/002625 A2 | 1/2007 | |
| WO | 2007/053736 A2 | 5/2007 | |
| WO | WO-2007053736 A2 * | 5/2007 | ............. C07C 17/38 |
| WO | 2007/079431 A2 | 7/2007 | |
| WO | 2008054781 A1 | 5/2008 | |
| WO | 2008054782 A1 | 5/2008 | |
| WO | 2008/121778 A1 | 10/2008 | |
| WO | 2009/003084 A1 | 12/2008 | |
| WO | 2009/003165 A1 | 12/2008 | |
| WO | 2009/018561 A2 | 2/2009 | |
| WO | 2009/021154 A2 | 2/2009 | |
| WO | 2009/089511 A2 | 7/2009 | |
| WO | 2009137656 A1 | 11/2009 | |
| WO | 2009137658 A2 | 11/2009 | |
| WO | WO-2009137658 A2 * | 11/2009 | ............. C09K 5/044 |
| WO | 2010/059685 A1 | 5/2010 | |
| WO | 2011/059078 A1 | 5/2011 | |

OTHER PUBLICATIONS

Papadimitriou, Physical Chemistry Chemical Physics, 2007, vol. 9, pp. 1-13.

Satterfield, Heterogeneous Catalysis in Industrial Practice, $2^{nd}$ edition, McGraw-Hill, New York, 1991, pp. 87-112.

Arkema France Notice of Opposition/Submission mailed Jul. 6, 2020.

Mexichem Notice of Opposition/Submission mailed Jul. 8, 2020.

Decision of Technical Board of Appeal 3.3.10 of Mar. 12, 2019 (Case T2172/16).

Specifications for Fluorocarbon Refrigerants, ARI 2006 Standard for Specifications, 2006, Arlington, VA.

ARTI Refrigerant Database, Data Summaries—vol. 1: Single-Compound Refrigerants, Sep. 1999, Arlington, VA.

\* cited by examiner

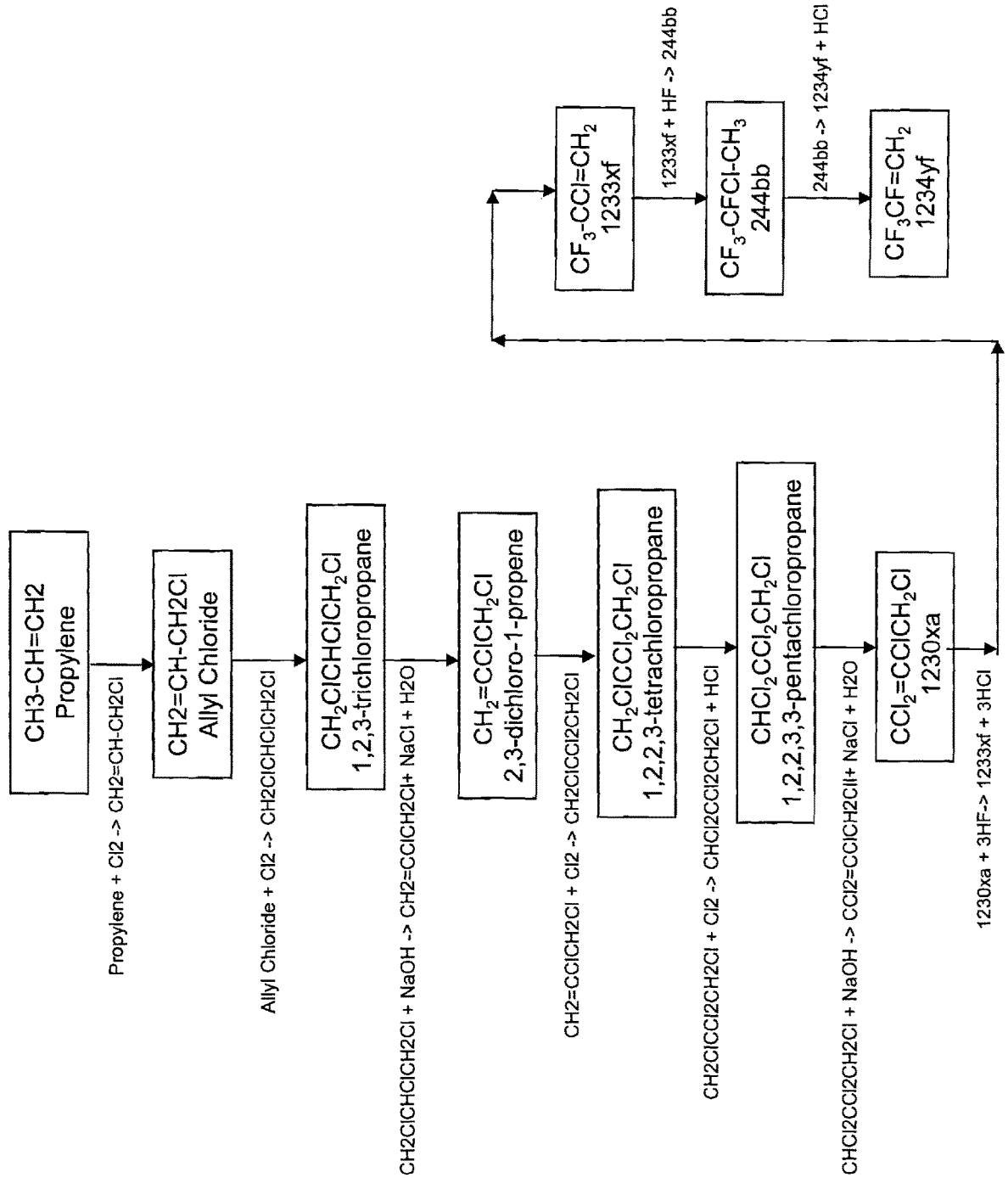

COMPOSITIONS COMPRISING 2,3,3,3-TETRAFLUOROPROPENE, 1,1,2,3-TETRA-CHLOROPROPENE, 2-CHLORO-3,3,3-TRIFLUOROPROPENE, OR 2-CHLORO-1,1,1,2-TETRAFLUOROPROPANE

FIELD OF THE INVENTION

The present disclosure relates to the field of compositions which may be useful as heat transfer compositions, aerosol propellants, foaming agents (blowing agents), solvents, cleaning agents, carrier fluids, displacement drying agents, buffing abrasion agents, polymerization media, foaming agents for polyolefins and polyurethane, gaseous dielectrics, extinguishing agents, and fire suppression agents in liquid or gaseous form. In particular, the present disclosure relates to compositions which may be useful as heat transfer compositions, such as 2,3,3,3-tetrafluoropropene (HFO-1234yf, or 1234yf) or the compositions comprising 1,1,1,2,3-pentafluoropropane (HFC-245eb, or 245eb) which are useful in processes to produce HFO-1234yf.

BACKGROUND OF THE INVENTION

New environmental regulations have led to the need for new compositions for use in refrigeration, air-conditioning and heat pump apparatus. Low global warming potential compounds are of particular interest.

SUMMARY OF THE INVENTION

Applicants have found that in preparing such new low global warming potential compounds, such as HFO-1234yf, that certain additional compounds are present in small amounts.

Therefore, in accordance with the present invention, there is provided a composition comprising HFO-1234yf and at least one additional compound selected from the group consisting of HCO-1250xf, HCC-260da, HCC-240aa, HCO-1230xa, HCFO-1233xf, HCFO-1233zd, HCFC-244bb, HCFC-244db, HFO-1234ze, HFC-245cb, HFO-1243zf, HCFO-1223za, HCFO-1224zb, HFO-1225zc, HCFC-241db, HCFC-242dc, HCFO-1232xf, HCFO-1231xf, and HCFO-1233yf. The composition may contain less than about 1 weight percent of the at least one additional compound, based on the total weight of the composition.

In addition, in accordance with the present invention, there is provided a composition comprising HCO-1230xa and at least one additional compound selected from the group consisting of propylene, HCO-1260zf, HCC-260da, HCC-260db, HCO-1250xf, HCC-250aa, and HCC-240aa.

In addition, in accordance with the present invention, there is provided a composition comprising HCFO-1233xf and at least one additional compound selected from the group consisting of propylene, HCO-1260zf, HCC-260da, HCC-260db, HCO-1250xf, HCC-250aa, HCC-240aa, HCO-1230xa, HFO-1243zf, HCFO-1223za, HCFO-1224zb, HFO-1225zc, HCFO-1233yf, HCFO-1232xf, HCFC-1231xf, HCFC-241db, and HCFC-242dc.

In addition, in accordance with the present invention, there is provided a composition comprising HCFC-244bb and at least one additional compound selected from the group consisting of propylene, HCO-1250xf, HCC-260da, HCC-260db, HCC-240aa, HCO-1230xa, HCFO-1233xf, HFO-1243zf, HCFO-1223az, HCFO-1224zb, HFO-1225zc, HCFC-241db, HCFC-242dc, HCFO-1232xf, HCFO-1231xf, and HCFC-1233yf.

BRIEF DESCRIPTION OF THE DRAWINGS

FIG. 1 shows a reaction sequence useful for formation of compositions of the present invention.

DETAILED DESCRIPTION

Compositions

HFO-1234yf (2,3,3,3-tetrafluoropropene) has been suggested for use as a refrigerant, heat transfer fluid, aerosol propellant, foam expansion agent, among other uses. It has also, advantageously, been found that HFO-1234yf has a low global warming potential (GWP) as reported by V. C. Papadimitriou, et al. in *Physical Chemistry Chemical Physics*, 2007, volume 9, pages 1-13. Thus, HFO-1234yf is a good candidate for replacing the higher GWP saturated HFC refrigerants.

In one embodiment, the present disclosure provides a composition comprising HFO-1234yf and at least one additional compound selected from the group consisting of HCO-1250xf, HCC-260da, HCC-260db, HCC-240aa, HCO-1230xa, HCFO-1233xf, HCFO-1233zd, HCFC-244bb, HCFC-244db, HFO-1234ze, HFC-245cb, HFO-1243zf, HCFO-1223za, HCFO-1224zb, HFO-1225zc, HCFC-241db, HCFC-242dc, HCFO-1232xf, HCFO-1231xf, and HCFO-1233yf.

The compositions of the present invention may comprise HFO-1234yf and one additional compound, or two additional compounds, or three or more additional compounds.

In another embodiment, the compositions of the present invention comprise HFO-1234yf and HCFO-1232xf.

In another embodiment, the compositions of the present invention comprise HFO-1234yf and at least one compound selected from HCFC-243db, HCFO-1233xf, HCFO-1231xf, HCFC-242dc and HCFC-241db.

In another embodiment, the compositions of the present invention comprise at least one compound selected from the group consisting of HCFC-243db and HFC-245fa.

In one embodiment, the total amount of additional compound(s) in the composition comprising HFO-1234yf ranges from greater than zero weight percent to less than 1 weight percent, based on the total weight of the composition. In another embodiment, the total amount of additional compound(s) ranges from greater than zero weight percent to less than 0.5 weight percent, based on the total weight of the composition.

In one embodiment, the compositions comprising HFO-1234yf and other compounds may further comprise a specific tracer compound, such as HFC-245cb. In this embodiment, the HFC-245cb tracer may be present at a concentration from about 1 part per million (ppm) to about 1000 ppm in the composition. In another embodiment, the HFC-245cb tracer may be present at a concentration from about 1 ppm to about 500 ppm. Alternatively, the HFC-245cb tracer may be present at a concentration from about 10 ppm to about 300 ppm.

The compositions disclosed herein comprising HFO-1234yf are useful as low global warming potential (GWP) heat transfer compositions, aerosol propellant, foaming agents, blowing agents, solvents, cleaning agents, carrier fluids, displacement drying agents, buffing abrasion agents, polymerization media, expansion agents for polyolefins and polyurethane, gaseous dielectrics, extinguishing agents, and fire suppression agents in liquid or gaseous form. The disclosed compositions can act as a working fluid used to carry heat from a heat source to a heat sink. Such heat transfer compositions may also be useful as a refrigerant in a cycle wherein the fluid undergoes a phase change; that is, from a liquid to a gas and back or vice versa.

Examples of heat transfer systems include but are not limited to air conditioners, freezers, refrigerators, heat pumps, water chillers, flooded evaporator chillers, direct expansion chillers, walk-in coolers, heat pumps, mobile refrigerators, mobile air conditioning units and combinations thereof.

As used herein, mobile refrigeration apparatus, mobile air conditioning or mobile heating apparatus refers to any refrigeration, air conditioner, or heating apparatus incorporated into a transportation unit for the road, rail, sea or air. In addition, mobile refrigeration or air conditioner units, include those apparatus that are independent of any moving carrier and are known as "intermodal" systems. Such intermodal systems include "containers' (combined sea/land transport) as well as "swap bodies" (combined road/rail transport).

As used herein, stationary heat transfer systems are systems associated within or attached to buildings of any variety. These stationary applications may be stationary air conditioning and heat pumps (including but not limited to chillers, high temperature heat pumps, residential, commercial or industrial air conditioning systems, and including window, ductless, ducted, packaged terminal, chillers, and those exterior but connected to the building such as rooftop systems). In stationary refrigeration applications, the disclosed compositions may be useful in high temperature, medium temperature, and/or low temperature refrigeration equipment including commercial, industrial or residential refrigerators and freezers, ice machines, self-contained coolers and freezers, flooded evaporator chillers, direct expansion chillers, walk-in and reach-in coolers and freezers, and combination systems. In some embodiments, the disclosed compositions may be used in supermarket refrigerator and/or freezer systems.

The compounds making up the disclosed compositions are defined in Table 1.

TABLE 1

| Code | Formula | Name |
|---|---|---|
|  |  | Propylene |
| HCO-1260zf | $CH_2=CHCH_2Cl$ | 3-chloropropene |
| HCO-1250xf | $CH_2=CClCH_2Cl$ | 2,3-dichloropropene |
| HCC-260da | $CH_2ClCHClCH_2Cl$ | 1,2,3-trichloropropane |
| HCC-260db | $CH_3CHClCHCl_2$ | 1,1,2-trichloropropane |
| HCC-250aa | $CH_2ClCCl_2CH_2Cl$ | 1,2,2,3-tetrachloropropane |
| HCC-240aa | $CHCl_2CCl_2CH_2Cl$ | 1,1,2,2,3-pentachloropropane |
| HCO-1230xa | $CCl_2=CClCH_2Cl$ | 1,1,2,3-tetrachloropropene |
| HCFO-1233xf | $CF_3CCl=CH_2$ | 2-chloro-3,3,3-trifluoropropene |
| HCFO-1233zd | $CF_3CH=CHCl$ | 1-chloro-3,3,3-trifluoropropene |
| HCFC-244bb | $CF_3CFClCH_3$ | 2-chloro-1,1,1,2-tetrafluoropropane |
| HCFC-244db | $CF_3CHClCH_2F$ | 2-chloro-1,1,1,3-tetrafluoropropane |
| HFO-1234ze | $CF_3CH=CHF$ | 1,3,3,3-tetrafluoropropene |
| H FC-245cb | $CF_3CF_2CH_3$ | 1,1,1,2,2-pentafluoropropane |
| HFO-1243zf | $CF_3CH=CH_2$ | 3,3,3-trifluoropropene |
| HCFO-1223za | $CF_3CH=CCl_2$ | 1,1-dichloro-3,3,3-trifluoropropene |
| HCFO-1224zb | $CF_3CH=CClF$ | 1-chloro-1,3,3,3-tetrafluoropropene |
| HFO-1225zc | $CF_3CH=CF_2$ | 1,1,3,3,3-pentafluoropropene |
| HCFC-241db | $CCl_2FCHClCH_2Cl$ | 1-chloro-1,1,2,3-tetrafluoropropane |
| HCFC-242dc | $CClF_2CHClCH_2Cl$ | 1,1-difluoro-1,2,3-trichloropropane |
| HCFO-1232xf | $CClF_2CCl=CH_2$ | 2,3-dichloro-3,3-difluoropropene |
| HCFO-1231xf | $CCl_2FCCl=CH_2$ | 2,3,3-trichloro-3-fluoropropene |
| HCFO-1233yf | $CClF_2CF=CH_2$ | 3-chloro-2,3,3-trifluoropropene |
| HCFC-243db | $CF_3CHClCH_2Cl$ | 2,3-dichloro-1,1,1-trifluoro-propane |
| HFC-245fa | $CF_3CH_2CHF_2$ | 1,1,1,3,3-pentafluoropropane |

HCFO-1233xf, HCFC-244bb, and many other compounds as listed in Table 1 are available from specialty chemical manufacturers, including SynQuest Laboratories, Inc. (Alachua, Fla., U.S.A.) or may be made by methods known in the art. For instance, HCFO-1233xf, and HCFC-244bb may be prepared by non-catalytic chlorination of HFO-1243zf, as described in International Patent Application Publication No. WO2008/054782, published May 8, 2008. Also, HCFO-1233xf and HCFC-244bb may be prepared by catalytic fluorination of HCFC-243db as described in International Patent Application Publication No. WO2008/054781, published May 8, 2008. The additional compounds present in each disclosed composition will depend upon the method of manufacture.

Alternatively, HCO-1230xa can be produced from 1,2,3-trichloropropane as described in US2007/0197842 A1. Additionally, disclosed in US2007/0197842 is the reaction of HCO-1230xa with HF in the presence of catalyst in the vapor phase to form HCFO-1233xf. Alternatively, HCFO-1233xf may also be produced by fluorination of 1,1,2,3-tetrachloropropene, (HCO-1230xa) with further fluorination forming HCFC-244bb and then dehydrochlorination forming HFO-1234yf, as described in US2009/0240090.

Certain of the compounds listed in Table 1 may exist in more than one isomer, in particular HFO-1234ze, HCFO-1233zd, and HCFO-1224zb. For instance, HFO-1234ze may exist as the E-isomer or Z-isomer. As used herein HFO-1234ze is intended to refer to either of the E-isomer, the Z-isomer or any mixtures of these isomers. As used herein HCFO-1233zd is intended to refer to either of the E-isomer, the Z-isomer or any mixtures of these isomers. As used herein HFO-1224zb is intended to refer to either of the E-isomer, the Z-isomer or any mixtures of these isomers.

In addition, in accordance with the present invention, there is provided a composition comprising HCO-1230xa and at least one additional compound selected from the group consisting of propylene, HCO-1260zf, HCO-260da, HCC-260db, HCO-1250xf, HCC-250aa, and HCC-240aa.

In another embodiment, the compositions of the present invention comprise HCO-1230xa and HCC-240aa. And in another embodiment, the compositions of the present invention may comprise HCO-1230xa, HCC-240aa, and at least one compound selected from the group consisting of HCC-250aa and HCC-260da.

In addition, in accordance with the present invention, there is provided a composition comprising HCFO-1233xf and at least one additional compound selected from the group consisting of propylene, HCO-1260zf, HCC-260da, HCC-260db, HCO-1250xf, HCC-250aa, HCC-240aa, HCO-1230xa, HFO-1243zf, HCFO-1223za, HCFO-1224zb, HFO-1225zc, HCFO-1233yf, HCFO-1232xf, HCFC-1231xf, HCFC-241db, and HCFC-242dc.

In another embodiment, the compositions of the present invention comprise HCO-1230xa and HCFO-1232xf. And in another embodiment the compositions of the present invention comprise, HCO-1230xa, HCFO-1232xf and HCFO-1231xf.

In addition, in accordance with the present invention, there is provided a composition comprising HCFC-244bb and at least one additional compound selected from the group consisting of propylene, HCO-1250xf, HCC-260da, HCC-260db, HCC-240aa, HCO-1230xa, HCFO-1233xf, HFO-1243zf, HCFO-1223az, HCFO-1224zb, HFO-1225zc, HCFC-241db, HCFC-242dc, HCFO-1232xf, HCFO-1231xf, and HCFC-1233yf.

In another embodiment, the compositions of the present invention comprising HCFC-244bb may further comprise at least one compound selected from the group consisting of HCFC-243db and HFC-245fa.

The series of reactions that may form the compositions of the present invention are shown in FIG. 1. The sequence of steps begins with the chorination of propylene by reaction with chlorine, $Cl_2$ to form allyl chloride or HCO-1260zf ($CH_2$=$CHCH_2Cl$). The next step involves further chlorination in the presence of $Cl_2$ to product HCC-260db ($CH_2ClCHClCH_2Cl$). Reaction of HCC-260db with aqueous NaOH (or other caustic solution) forms HCO-1250xf ($CH_2$=$CClCH_2Cl$). And reaction of HCO-1250xf with chlorine, $Cl_2$ produces HCC-250aa ($CH_2ClCCl_2CH_2Cl$, or 1,2,2,3-tetrachloropropane). Further chlorination with $Cl_2$ will produce HCC-240da ($CHCl_2CCl_2CH_2Cl$). Reaction of HCC-240da with aqueous NaOH (or other caustic solution) will form HCO-1230xa ($CCl_2$=$CClCH_2Cl$).

In another embodiment, any of the compositions as described previously may additionally comprise hydrogen fluoride (HF), due to the presence of HF as either a reactant or a by-product of the reaction chemistry to produce each composition.

Of note are compositions which are free of HCl, compositions which are free of HF and compositions which are free of both HCl and HF. Of particular note are compositions which are acid free. Acids can be removed by processes known in the art such as distillation and water or caustic washing.

Fluorination of HCO-1230xa

The HCO-1230xa may be fluorinated by reaction with hydrogen fluoride (HF) in the presence of a catalyst to produce HCFO-1233xf. This reaction is shown in FIG. 1.

The fluorochlorination reaction may be carried out in the liquid or vapor phase. For liquid phase embodiments of the invention, the reaction of HCO-1230xa with HF may be conducted in a liquid-phase reactor operating in batch, semi-batch, semi-continuous, or continuous modes. In the batch mode, HCO-1230xa and HF are combined in an autoclave or other suitable reaction vessel and heated to the desired temperature.

In one embodiment, this reaction is carried out in semi-batch mode by feeding HCO-1230xa to a liquid-phase reactor containing HF. In another embodiment, HF may be fed to a liquid-phase reactor containing a mixture of HCO-1230xa and reaction products formed by reacting HF and HCO-1230xa. In another embodiment of the liquid-phase process, HF and HCO-1230xa may be fed concurrently in the desired stoichiometric ratio to the reactor containing a mixture of HF and reaction products formed by reacting HF and HCO-1230xa.

Suitable temperatures for the reaction of HF with HCO-1230xa in the liquid-phase reactor are, in one embodiment, from about 80° C. to about 180° C., and in another embodiment, from about 100° C. to about 150° C. Higher temperatures typically result in greater conversion of the HCO-1230xa.

A suitable molar ratio of HF to total amount of HCO-1230xa fed to the liquid-phase reactor is, in one embodiment, at least stoichiometric (about 3:1, HF to HCO-1230xa) and in another embodiment, is from about 5:1 to about 100:1. Of note are embodiments wherein the molar ratio of HF to HFO-1243zf is from about 8:1 to about 50:1.

The reactor pressure in the liquid-phase process is not critical and in batch reactions is usually the autogenous pressure of the system at the reaction temperature. The pressure of the system increases as hydrogen chloride is formed by replacement of hydrogen substituents by chlorine, and by replacement of chlorine substituents by fluorine in the starting materials and intermediate reaction products. In a continuous process it is possible to set the pressure of the reactor in such a way that the lower boiling products of the reaction are vented from the reactor, optionally through a packed column or condenser. In this manner, higher boiling intermediates remain in the reactor and the volatile products are removed. Typical reactor pressures are from about 20 psig (239 kPa) to about 1,000 psig (6,994 kPa).

In some embodiments, in which the reaction is conducted using a liquid-phase process, catalysts which may be used include carbon, $AlF_3$, $BF_3$, $FeCl_{3-a}F_a$ (where a=0 to 3), $FeX_3$ supported on carbon, $SbCl_{3-a}F_a$, AsF3, $MCl_{5-b}F_b$ (where b=0 to 5 and M=Sb, Nb, Ta, or Mo), and $M'Cl_{4-c}F_c$ (where c=0 to 4, and M'=Sn, Ti, Zr, or Hf). In another embodiment, catalysts for the liquid phase process are $MCl_{5-b}F_b$ (where b=0 to 5 and M=Sb, Nb, or Ta).

In another embodiment, the reaction of HF with HCO-1230xa is carried out in the vapor phase. Typically a heated reactor is used. A number of reactor configurations are possible including horizontal or vertical orientation of the reactor as well as the sequence of reaction of the HCO-1230xa with HF. In one embodiment of the invention, the HCO-1230xa may be initially vaporized and fed to the reactor as a gas.

Suitable temperatures for the vapor-phase reaction are from about 120° C. to about 500° C. Higher temperatures result in greater conversion of HCO-1230xa and higher degrees of fluorination and halogenation in the converted compounds.

Suitable reactor pressures for the vapor-phase reactor may be from about 1 to about 30 atmospheres. A pressure of about 15 to about 25 atmospheres may be advantageously employed to facilitate separation of HCl from other reaction products, and the suitable reaction time may vary from about 1 to about 120 seconds, preferably from about 5 to about 60 seconds.

The molar ratio of HF to the total amount of HCO-1230xa for the vapor-phase reaction is, in one embodiment, from about the stoichiometric ratio of HF to the total amount of HCO-1230xa (3:1 HF to HCO-1230xa) to about 50:1 and, in another embodiment, from about 10:1 to about 30:1.

In one embodiment, a catalyst is used in the reaction zone for the vapor-phase reaction of HF with (3:1 HF to HCO-1230xa). Chlorofluorination catalysts which may be used in the vapor phase reaction include carbon; graphite; alumina; fluorided alumina; aluminum fluoride; alumina supported on carbon; aluminum fluoride supported on carbon; fluorided alumina supported on carbon; magnesium fluoride supported on aluminum fluoride; metals (including elemental metals, metal oxides, metal halides, and/or other metal salts); metals supported on aluminum fluoride; metals supported on fluorided alumina; metals supported on alumina; and metals supported on carbon; mixtures of metals.

Suitable metals for use as catalysts (optionally supported on alumina, aluminum fluoride, fluorided alumina, or carbon) include chromium, iron, cobalt, nickel, ruthenium, rhodium, palladium, osmium, iridium, platinum, manganese, rhenium, scandium, yttrium, lanthanum, titanium, zirconium, and hafnium, copper, silver, gold, zinc, and/or metals having an atomic number of 58 through 71 (i.e., the lanthanide metals). In one embodiment, when used on a support, the total metal content of the catalyst will be from about 0.1 to about 20 percent by weight based on the total weight of the catalyst; in another embodiment from about 0.1 to about 10 percent by weight based on the total weight of the catalyst.

Suitable chlorofluorination catalysts for the vapor-phase reactions include chromium-containing catalysts including chromium(III) oxide ($Cr_2O_3$); $Cr_2O_3$ with other metals such as magnesium halides or zinc halides supported on $Cr_2O_3$; chromium(III) halides supported on carbon; mixtures of chromium and magnesium (including elemental metals, metal oxides, metal halides, and/or other metal salts) optionally supported on graphite; and mixtures of chromium and other metals (including elemental metals, metal oxides, metal halides, and/or other metal salts) optionally supported on graphite, alumina, or aluminum halides such as aluminum fluoride.

Chromium-containing catalysts are well known in the art. They may be prepared by either precipitation methods or impregnation methods as generally described by Satterfield on pages 87-112 in *Heterogeneous Catalysis in Industrial Practice*, $2^{nd}$ edition (McGraw-Hill, New York, 1991).

Of note are chlorofluorination catalysts that comprise at least one chromium-containing component selected from the group consisting of crystalline alpha-chromium oxide where from about 0.05 atom % to about 6 atom % of the chromium atoms in the alpha-chromium oxide lattice are replaced by trivalent cobalt atoms, and crystalline alpha-chromium oxide where from about 0.05 atom % to about 6 atom % of the chromium atoms in the alpha-chromium oxide lattice are replaced by trivalent cobalt atoms which has been treated with a fluorinating agent. These catalysts, including their preparation, have been disclosed in U.S. Patent Application Publication US2005/0228202.

In another embodiment, the vapor phase catalyst for reaction of HCO-1230xa with HF may be a catalyst composition comprising $Cr_2O_3$ prepared by pyrolysis of $(NH_4)_2Cr_2O_7$ as described in U.S. Pat. No. 5,036,036.

Optionally, the metal-containing catalysts described above can be pretreated with HF. This pretreatment can be accomplished, for example, by placing the metal-containing catalyst in a suitable container, and thereafter, passing HF over the metal-containing catalyst. In one embodiment, such container can be the reactor used to perform the chlorofluorination reaction. In one embodiment, the pretreatment time is from about 15 to about 300 minutes, and the pretreatment temperature is from about 200° C. to about 450° C.

Fluorination of HCFO-1233xf

In some embodiments, HCFO-1233xf may be used to make HCFC—HCFC-244bb, and/or HFO-1234yf by fluorination. These reactions are shown in FIG. 1.

In one embodiment, the reaction of HCFO-1233xf to HCFC-244bb may be carried out in the liquid phase. In another embodiment, the reaction may be carried out in the vapor phase.

In one embodiment, the reaction of HCFO-1233xf to HCFC-244bb may be carried out in batch mode. In another embodiment, the reaction may be carried out in a continuous mode.

In one embodiment, a liquid phase reaction of HCFO-1233xf to HCFC-244bb may be carried out in the presence of a catalyst. In one embodiment, the catalyst may be a Lewis acid catalyst. In one embodiment, the catalyst may be a metal-halide catalyst. In another embodiment, the catalyst may be at least one catalyst selected from the group consisting of antimony halides, tin halides, thallium halides, iron halides and combinations of two or more thereof. In another embodiment, the catalysts may be at least one catalyst selected from antimony pentachloride ($SbCl_5$), antimony trichloride ($SbCl_3$), antimony pentafluoride ($SbF_5$), tin tetrachloride ($SnCl_4$), titanium tetrachloride ($TiCl_4$), iron trichloride ($FeCl_3$, and combinations thereof. In some embodiments, the reaction may be carried out with any known fluorination catalyst for liquid phase reactions.

In one embodiment, the reaction of HCFO-1233xf to HCFC-244bb may be carried out in the absence of catalyst.

In one embodiment, a vapor phase reaction of HCFO-1233xf to HCFC-244bb may be carried out in the presence of a catalyst. In one embodiment, the reaction is carried out in the presence of a chromium-based catalyst, an iron-based catalyst, or combinations thereof. In one embodiment, the chromium based catalyst is a chromium oxide (e.g. $Cr_2O_3$). In one embodiment, the iron-based catalyst may be $FeCl_3$ on carbon.

In one embodiment, the vapor phase reaction of HCFO-1233xf to HCFC-244bb is carried out in the absence of catalyst.

Dehydrochlorination of HCFC-244bb

In some embodiments, dehydrochlorination of HCFC-244bb is used to prepare HFO-1234yf.

In one embodiment, dehydrochlorination of HCFC-244bb to HFO-1234yf is carried out in the vapor phase.

In one embodiment, vapor phase dehydrochlorination is carried out in the presence of catalyst. In one embodiment, the catalyst is selected from carbon and/or metal based catalysts. In one embodiment, the catalyst may be selected from an activated carbon, a nickel-based catalyst, a palladium based catalyst, or any combination of these catalysts. In one embodiment, the catalyst may be selected from the group consisting of Ni-mesh, palladium on carbon, palladium on aluminum oxide, or combinations thereof.

In one embodiment, the catalyzed vapor phase dehydrochlorination is carried out at a temperature from about 200 to 600° C. In another embodiment, the catalytic vapor phase dehydrochlorination is carried out at a temperature from about 250 to 500° C. The reaction pressure is about from 0 to 150 psi.

In another embodiment, HFO-1234yf is prepared by thermal dehydrochlorination of HCFC-244bb. In one embodiment, this reaction occurs in the absence of a catalyst. In one embodiment, HCFC-244bb is introduced into a reaction vessel which temperature is maintained at a temperature high enough to effect the thermal dehydrochlorination of HCFC-244bb. In one embodiment, the temperature is high enough to effect the thermal dehydrochlorination of HCFC-244bb to a percent conversion of at least 50%. In another embodiment, the temperature is high enough to effect the thermal dehydrochlorination of HCFC-244bb to a percent conversion of at least 65%. In yet another embodiment, the temperature is high enough to effect the thermal dehydrochlorination of HCFC-244bb to a percent conversion of at least 80%. In yet another embodiment, the temperature is high enough to effect the thermal dehydrochlorination of HCFC-244bb to a percent conversion of at least 70% for at least 12 hours of continuous operation.

In one embodiment, HCFC-244bb is introduced into a reaction vessel into a reaction vessel which temperature is maintained at a temperature in the range of from about 500° C. to about 700° C. In another embodiment, the temperature of the reaction vessel is maintained in the range from about 500° C. to about 650° C. In yet another embodiment, the temperature of the reaction vessel is maintained at a temperature high enough to effect the pyrolysis of HCFC-244bb to HFO-1234yf with a selectivity of 80% or greater. In yet another embodiment, the temperature of the reaction vessel is maintained at a temperature high enough to effect the pyrolysis of HCFC-244bb to HFO-1234yf with a selectivity of 85% or greater.

In one embodiment, for either the catalyzed or non-catalytic dehydrochlorination reaction, the reaction zone is a reaction vessel comprised of materials which are resistant to corrosion. In one embodiment, these materials comprise alloys, such as nickel-based alloys such as HasteHoy®, nickel-chromium alloys commercially available from Special Metals Corp. under the trademark Inconel® (hereinafter "Inconel®") or nickel-copper alloys commercially available from Special Metals Corp. (New Hartford, N.Y.) under the trademark Monel®, or vessels having fluoropolymers linings.

In one embodiment, the HCFC-244bb is preheated in a vaporizer to a temperature of from about 30° C. to about 100° C. In another embodiment, the HCFC-244bb is preheated in a vaporizer to a temperature of from about 30° C. to about 80° C.

In some embodiments, an inert diluent gas is used as a carrier gas for HCFC-244bb. In one embodiment, the carrier gas is selected is nitrogen, argon, helium or carbon dioxide.

Without further elaboration, it is believed that one skilled in the art can, using the description herein, utilize the present invention to its fullest extent. The following specific embodiments are, therefore, to be construed as merely illustrative, and do not constrain the remainder of the disclosure in any way whatsoever.

Utility

The compositions disclosed herein comprising HFO-1234yf are useful as low global warming potential (GWP) heat transfer compositions, aerosol propellant, foam expansion agents (also known as foaming agents or blowing agents), solvents, cleaning agents, carrier fluids, displacement drying agents, buffing abrasion agents, polymerization media, foaming agents for polyolefins and polyurethane, gaseous dielectrics, extinguishing agents, and fire suppression agents in liquid or gaseous form. The disclosed compositions can act as a working fluid used to carry heat from a heat source to a heat sink. Such heat transfer compositions may also be useful as a refrigerant in a cycle wherein the fluid undergoes a phase change; that is, from a liquid to a gas and back or vice versa.

Examples of heat transfer systems include but are not limited to air conditioners, freezers, refrigerators, heat pumps, water chillers, flooded evaporator chillers, direct expansion chillers, walk-in coolers, heat pumps, mobile refrigerators, mobile air conditioning units and combinations thereof.

In one embodiment, the compositions comprising HFO-1234yf are useful in mobile heat transfer systems, including refrigeration, air conditioning, or heat pump systems or apparatus. In another embodiment, the compositions are useful in stationary heat transfer systems, including refrigeration, air conditioning, or heat pump systems or apparatus.

As used herein, mobile heat transfer systems refers to any refrigeration, air conditioner, or heating apparatus incorporated into a transportation unit for the road, rail, sea or air. In addition, mobile refrigeration or air conditioner units, include those apparatus that are independent of any moving carrier and are known as "intermodal" systems. Such intermodal systems include "containers' (combined sea/land transport) as well as "swap bodies" (combined road/rail transport).

As used herein, stationary heat transfer systems are systems that are fixed in place during operation. A stationary heat transfer system may be associated within or attached to buildings of any variety or may be stand alone devices located out of doors, such as a soft drink vending machine. These stationary applications may be stationary air conditioning and heat pumps (including but not limited to chillers, high temperature heat pumps, residential, commercial or industrial air conditioning systems, and including window, ductless, ducted, packaged terminal, chillers, and those exterior but connected to the building such as rooftop systems). In stationary refrigeration applications, the disclosed compositions may be useful in high temperature, medium temperature and/or low temperature refrigeration equipment including commercial, industrial or residential refrigerators and freezers, ice machines, self-contained coolers and freezers, flooded evaporator chillers, direct expansion chillers, walk-in and reach-in coolers and freezers, and combination systems. In some embodiments, the disclosed compositions may be used in supermarket refrigerator systems.

Therefore in accordance with the present invention, the compositions as disclosed herein containing HFO-1234yf may be useful in methods for producing cooling, producing heat, and transferring heat.

The compositions disclosed herein may be useful as low global warming potential (GWP) replacements for currently used refrigerants, including but not limited to R134a (or HFC-134a, 1,1,1,2-tetrafluoroethane), R22 (or HCFC-22, chlorodifluoromethane), R12 (CFC-12, dichlorodifluoromethane); R407C (ASHRAE designation for a blend of 52 weight percent R134a, 25 weight percent R125 (pentafluoroethane), and 23 weight percent R32 (difluoromethane)); R410A (ASHRAE designation for a blend of 50 weight percent R125 and 50 weight percent R32); and R404A (ASHRAE designation for a blend of 44 weight percent R125, 52 weight percent R143a (1,1,1-trifluoroethane), and 4.0 weight percent R134a), among others.

In many applications, some embodiments of the present compositions comprising HFO-1234yf are useful as refrigerants and provide at least comparable cooling performance (meaning cooling capacity and energy efficiency) as the refrigerant for which a replacement is being sought.

In another embodiment is provided a method for recharging a heat transfer system that contains a refrigerant to be replaced and a lubricant, said method comprising removing the refrigerant to be replaced from the heat transfer system while retaining a substantial portion of the lubricant in said system and introducing one of the present compositions comprising HFO-1234yf to the heat transfer system.

In another embodiment, a heat exchange system containing any of the present compositions comprising HFO-1234yf is provided, wherein said system is selected from the group consisting of air conditioners, freezers, refrigerators, heat pumps, water chillers, flooded evaporator chillers, direct expansion chillers, walk-in coolers, heat pumps, mobile refrigerators, mobile air conditioning units, and systems having combinations thereof. Additionally, the compositions comprising HFO-1234yf may be useful in secondary loop systems wherein these compositions serve as the primary refrigerant thus providing cooling to a secondary heat transfer fluid that thereby cools a remote location.

Vapor-compression refrigeration, air-conditioning, or heat pump systems include an evaporator, a compressor, a condenser, and an expansion device. A vapor-compression cycle re-uses refrigerant in multiple steps producing a cooling effect in one step and a heating effect in a different step. The cycle can be described simply as follows. Liquid refrigerant enters an evaporator through an expansion device, and the liquid refrigerant boils in the evaporator, by withdrawing heat from the environment, at a low temperature to form a gas and produce cooling. The low-pressure gas enters a compressor where the gas is compressed to raise its pressure and temperature. The higher-pressure (compressed) gaseous refrigerant then enters the condenser in which the refrigerant condenses and discharges its heat to the environment. The refrigerant returns to the expansion device through which the liquid expands from the higher-pressure level in the condenser to the low-pressure level in the evaporator, thus repeating the cycle.

In one embodiment, there is provided a heat transfer system containing any of the present compositions comprising HFO-1234yf. In another embodiment is disclosed a refrigeration, air-conditioning or heat pump apparatus containing any of the present compositions comprising HFO-1234yf. In another embodiment, is disclosed a stationary refrigeration or air-conditioning apparatus containing any of the present compositions comprising HFO-1234yf. In yet another embodiment is disclosed a mobile refrigeration or air conditioning apparatus containing a composition as disclosed herein.

In another embodiment, a method is provided for producing cooling comprising evaporating any of the present compositions comprising HFO-1234yf in the vicinity of a body to be cooled, and thereafter condensing said composition.

In another embodiment, a method is provided for producing heat comprising condensing any of the present compositions comprising HFO-1234yf in the vicinity of a body to be heated, and thereafter evaporating said compositions.

In another embodiment, disclosed is a method of using the present compositions comprising HFO-1234yf as a heat transfer fluid composition. The method comprises transporting said composition from a heat source to a heat sink.

In another embodiment, the present invention relates to foam expansion agent compositions comprising HFO-1234yf for use in preparing foams. In other embodiments the invention provides foamable compositions, and preferably thermoset (like polyurethane, polyisocyanurate, or phenolic) foam compositions, and thermoplastic (like polystyrene, polyethylene, or polypropylene) foam compositions and method of preparing foams. In such foam embodiments, one or more of the present compositions comprising HFO-1234yf are included as a foam expansion agent in foamable compositions, which composition preferably includes one or more additional components capable of reacting and/or mixing and foaming under the proper conditions to form a foam or cellular structure.

The present invention further relates to a method of forming a foam comprising: (a) adding to a foamable composition a composition comprising HFO-1234yf of the present invention; and (b) processing the foam able composition under conditions effective to form a foam.

Another embodiment of the present invention relates to the use of the compositions of the present invention comprising HFO-1234yf as propellants in sprayable compositions. Additionally, the present invention relates to a sprayable compositions comprising HFO-1234yf. The active ingredient to be sprayed together with inert ingredients, solvents and other materials may also be present in a sprayable composition. In one embodiment, a sprayable composition is an aerosol. The present compositions can be used to formulate a variety of industrial aerosols or other sprayable compositions such as contact cleaners, dusters, lubricant sprays, mold release sprays, insecticides, and the like, and consumer aerosols such as personal care products (such as, e.g., hair sprays, deodorants, and perfumes), household products (such as, e.g., waxes, polishes, pan sprays, room fresheners, and household insecticides), and automotive products (such as, e.g., cleaners and polishers), as well as medicinal materials such as anti-asthma and anti-halitosis medications. Examples of this includes metered dose inhalers (MDIs) for the treatment of asthma and other chronic obstructive pulmonary diseases and for delivery of medicaments to accessible mucous membranes or intranasally The present invention further relates to a process for producing aerosol products comprising the step of adding a composition of the present invention comprising HFO-1234yf to a formulation, including active, ingredients in an aerosol container, wherein said composition functions as a propellant. Additionally, the present invention further relates to a process for producing aerosol products comprising the step of adding a composition of the present invention comprising HFO-1234yf to a barrier type aerosol package (like a bag-in-a-can or piston can) wherein said composition is kept separated from other formulation ingredients in an aerosol container, and wherein said composition functions as a propellant. Additionally, the present invention further relates to a process for producing aerosol products comprising the step of adding only a composition of the present invention comprising HFO-1234yf to an aerosol package, wherein said composition functions as the active ingredient (e.g., a duster, or a cooling or freezing spray).

The compositions disclosed herein comprising HCO-1230xa, HCFO-1233xf, and HCFC-244bb are useful in methods to prepare HFO-1234yf as described previously herein.

Without further elaboration, it is believed that one skilled in the art can, using the description herein, utilize the present invention to its fullest extent. The following specific embodiments are, therefore, to be construed as merely illustrative, and do not constrain the remainder of the disclosure in any way whatsoever.

EXAMPLES

General Procedure for Product Analysis

The following general procedure is illustrative of the method used for analyzing the products of fluorination reactions. Part of the total reactor effluent was sampled on-line for organic product analysis using a gas chromatograph equipped with a mass selective detector (GC/MS). The gas chromatography utilized a 20 ft. (6.1 m) long×⅛ in. (0.32 cm) diameter tube containing perfluorinated polyether sold under the trademark Krytox® by E. I. du Pont de Nemours and Company (hereinafter "DuPont") of Wilmington, Del. on an inert carbon support. The helium flow was 30 mL/min ($5.0 \times 10^{-7}$ m$^3$/sec). Gas chromatographic conditions were 60° C. for an initial hold period of three minutes followed by temperature programming to 200° C. at a rate of 6° C./minute.

Example 1

Fluorination of HCFO-1233xf to HCFC-244bb

The contents of a small PTFE vial containing 20 grams of viscous SbF$_5$ were poured into a dry 400 mL Hastelloy® shaker tube. The tube was closed and was pressurized with nitrogen for leak testing. The shaker tube was then cooled to less than −40° C. with dry ice, slowly vented, and then evacuated. 75 grams (3.75-moles) of anhydrous HF was condensed into the shaker tube followed by 165 grams (1.26-moles) of HCFO-1233xf. The shaker tube was placed in a barricade and shaking was started.

The shaker tube was agitated at ambient temperature (~20-23° C.) and the pressure was 21 to 25 psig. After 2 hours, shaking was stopped and 150 mL of water was carefully pumped into the shaker tube. The tube was left overnight and then cooled to 0 to 5° C. in an ice bath before depressurization and transferring the contents to a plastic container. The container was kept on ice.

The container contents were poured into a polypropylene separatory funnel containing some ice. The lower organic layer was light amber in appearance. The organic layer was separated into a media bottle made of a glass sold under the trademark of Pyrex® by Corning (Lowell, Mass.) (hereinafter "Pyrex®") containing ~50-mL of 4 molar (pH 7) phosphate buffer and ice (~100-mL). The organic layer was again separated and poured into a dry Pyrex® media bottle containing a small amount of anhydrous magnesium sulfate. Crude yield was 164.3 grams (about 120-mL, 86%).

GC/MS of the crude material showed that it was mostly HCFC-244bb. Other components included 0.16% 1233xf, and other byproducts totaling 12.2%.

Example 2

Fluorination of HCFO-1233xf to HCFC-244bb

The contents of a small PTFE vial containing 20 grams of viscous SbF$_5$ were poured into a dry 400-mL Hastelloy® shaker tube. The tube was closed and was pressurized with nitrogen for leak testing. The shaker tube was then cooled to less than −40° C. with dry ice, slowly vented, and then evacuated. 53 grams (2.65 moles) of anhydrous HF was transferred into the shaker tube followed by 227 grams (1.74 moles) of HCFO-1233xf was condensed into the chilled shaker tube. The shaker tube was placed in the barricade and shaking was started.

The shaker tube was agitated at ambient temperature (~18-21° C.) and the pressure was 16 to 20 psig. After 2 hours, shaking was stopped and 100 mL of water was carefully pumped into the shaker tube. The tube was left overnight and cooled to 0 to 5° C. in an ice bath before venting and transferring the contents to a plastic container. The container was kept on ice.

The container contents were poured into a polypropylene separatory funnel containing some ice. The lower organic layer was light amber in appearance. The organic layer was separated into a Pyrex® media bottle containing about 50 mL of 4 molar (pH 7) phosphate buffer and ice (~100-mL). The organic layer was again separated and poured into a dry Pyrex® media bottle containing a small amount of anhydrous magnesium sulfate. Crude yield was 238.8 grams (about 170-mL, 91%).

GC/MS of the crude material indicated that it was mostly HCFC-244bb. Other components included 0.11% HFC-245cb, 0.10% HFC-245eb, 0.26% HCFO-1233xf, and other byproducts totaling 9.7%.

Example 3

Example 3 demonstrates the conversion of HCFC-244bb (2-chloro-1,1,1,2-tetrafluoropropane) to HFO-1234yf (2,3,3,3-tetrafluoropropene) in the absence of a catalyst.

An empty Inconel® tube (½ inch OD) with a heated zone of about 12 inches was heated to a temperature between 500° C. and 626° C., and HFC-244bb was fed at 0.52 mL/hour through a vaporizer set at 40° C. using a N$_2$ sweep of 2.4 sccm (4.0×10$^{-8}$ m$^3$). The reactor effluent was analyzed using an on-line GCMS, with the results being reported in mole percent.

TABLE 2

| Temp., | Mole Percent | | | |
|---|---|---|---|---|
| ° C. | 1234yf | 244bb | 1233xf | Other |
| 500 | 14.2 | 82.6 | 1.2 | 2.0 |
| 550 | 57.0 | 35.4 | 1.2 | 6.4 |
| 574 | 77.0 | 13.0 | 1.4 | 8.6 |
| 603 | 85.0 | 1.3 | 0.7 | 13.0 |
| 626 | 82.5 | 0.2 | 1.4 | 15.9 |

Example 4

Example 4 demonstrates the conversion of HCFC-244bb (2-chloro-1,1,1,2-tetrafluoropropane) to HFO-1234yf (2,3,3,3-tetrafluoropropane) in the absence of a catalyst.

An empty Inconel® tube (½ inch OD) with a heated zone of about 12 inches was heated to 575° C., and HFC-244bb was fed at 0.35 mL/hour through a vaporizer set at 40° C. using a N$_2$ sweep of 3.6 sccm (6.0×10$^{-8}$ m$^3$). The reactor was operated for a total of 19 hours continuously, and samples were taken periodically and analyzed to determine % conversion of HFC-244bb, and selectivity to HFO-1234yf. The reactor effluent was analyzed using an on-line GCMS, and the data in Table 6 below is an average of at least two on-line injections at a given condition; the percentages are mole percent.

TABLE 3

| Hours | 1234yf | 244bb | 1233xd | 1223 (2 isomers) | Other |
|---|---|---|---|---|---|
| 3 | 68.8 | 17.9 | 5.1 | 0.5 | 7.7 |
| 4 | 61.5 | 22.7 | 7.4 | 1.1 | 7.3 |
| 8 | 61.1 | 15.0 | 14.1 | 3.9 | 5.9 |
| 12 | 60.1 | 13.7 | 16.4 | 6.0 | 9.8 |
| 15 | 66.9 | 14.5 | 12.0 | 2.7 | 3.9 |
| 19 | 67.4 | 7.0 | 16.6 | 8.2 | 0.8 |

Example 5

Example 5 demonstrates the dehydrochlorination of HCFC-244bb (2-chloro-1,1,1,2-tetrafluoropropane) in the presence of an activated carbon catalyst.

An Inconel® tube (½ inch OD) was filled with 4 cc (1.99 gm) of acid washed PCB Polynesian coconut shell based carbon from Calgon (6-10 mesh). HFC-244bb was fed at 1.04 mL/hour through a vaporizer set at 40° C. using a N$_2$ sweep of 2.4 sccm (4.0×10$^{-8}$ m$^3$) giving a total contact time of about 32 seconds while controlling the reactor temperature at 400° C.

The data in Table 4 shows the reactor effluent composition in mole percent for this process run with an activated carbon catalyst to make HFC-1234yf via HCl elimination over the period of 7 hours of operation.

TABLE 4

| Hours | 1234yf | 244bb | 1233xf | Other |
|---|---|---|---|---|
| 1 | 52.2 | 22.4 | 10.3 | 15.1 |
| 2 | 44.5 | 24.6 | 13.4 | 17.5 |
| 3 | 38.0 | 31.9 | 14.8 | 15.3 |
| 4 | 25.9 | 41.8 | 15.7 | 16.6 |

TABLE 4-continued

| Hours | 1234yf | 244bb | 1233xf | Other |
|---|---|---|---|---|
| 5 | 15.5 | 49.4 | 17.9 | 17.2 |
| 6 | 7.1 | 53.8 | 18.0 | 21.1 |
| 7 | 2.9 | 54.2 | 17.3 | 25.6 |

What is claimed is:

1. A composition comprising 1234yf and additional compounds wherein the additional compounds comprise:
   i) at least one member selected from the group consisting of 243db, HFC-245fa, HCFO-1233zd, HCFC-244bb, HCFC-244db, HFO-1234ze, HFO-1243zf, HCFO-1223za, HCFO-1224zb, and HFO-1225zc;
   ii) at least one member selected from the group consisting of HCO-1250xf, HCC-260da, HCC-240aa, 1230xa, and HCFO-1231xf; and
   iii) at least one member selected from the group consisting of 1231xf, HCFC-241db, and HCFC-242dc, and wherein the amount of the additional compounds is greater than 0 and less than 1 wt. %.

2. The composition of claim 1 wherein the composition comprises a refrigerant.

3. A composition comprising HCFO-1233xf, HFO-1243zf and additional compounds wherein the additional compounds comprise:
   i) at least one member selected from the group consisting of HCO-1230xa, HCFO-1223za, HCFO-1224zb, HFO-1225zc, HCFO-1233yf, 1234yf, 1231xf, and propylene; and,
   ii) at least one member selected from the group consisting of HCO-1260zf, HCC-260da, HCC-260db, HCO-1250xf, HCC-250aa, HOC-240aa, 245cb, HCO-1230xa, HCFO-1223za, HFO-1225zc, HCFO-1233yf, 1234yf, 1231xf, HCFC-241db, and HCFC-242dc, and propylene, and wherein the amount of the additional compounds is greater than 0 and less than 1 wt. %.

4. A method for producing cooling comprising evaporating a composition of claim 2 in the vicinity of a body to be cooled, and thereafter condensing said composition.

5. A method for producing heat comprising condensing a composition of any of claim 2 in the vicinity of a body to be heated, and thereafter evaporating said compositions.

6. The method of claim 4 wherein the method comprises operating a mobile refrigeration apparatus.

7. The method of claim 4 wherein the method comprises operating a stationary refrigeration apparatus.

8. The method of claim 4 wherein the method comprises operating a mobile air conditioning apparatus.

9. The composition of claim 3 further comprising at least one catalyst.

* * * * *